United States Patent
Martin et al.

(10) Patent No.: US 6,962,941 B2
(45) Date of Patent: Nov. 8, 2005

(54) TRYPTASE INHIBITORS

(75) Inventors: Thomas Martin, Constance (DE); Wolf-Rüdiger Ulrich, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/480,925

(22) PCT Filed: Jun. 14, 2002

(86) PCT No.: PCT/EP02/06537

§ 371 (c)(1),
(2), (4) Date: Dec. 16, 2003

(87) PCT Pub. No.: WO02/102771

PCT Pub. Date: Dec. 27, 2002

(65) Prior Publication Data

US 2004/0176421 A1 Sep. 9, 2004

(30) Foreign Application Priority Data

Jun. 19, 2001 (EP) .............................. 01114642

(51) Int. Cl.$^7$ ................... A61K 31/4025; C07D 403/12
(52) U.S. Cl. ................. 514/422; 548/518; 548/469; 548/361.1; 546/208; 546/276.4; 514/326; 514/343
(58) Field of Search ................ 514/422, 326, 514/343; 548/518, 469, 361.1; 546/208, 276.4

(56) References Cited

U.S. PATENT DOCUMENTS

| 6,489,327 B1 | 12/2002 | Bär et al. |
| 6,613,769 B1 | 9/2003 | Bode et al. |

FOREIGN PATENT DOCUMENTS

| WO | WO 95/32945 | 12/1995 |
| WO | WO 96/09297 | 3/1996 |
| WO | WO 98/04537 | 2/1998 |
| WO | WO99/12918 | 3/1999 |
| WO | WO 99/24395 | 5/1999 |
| WO | WO 99/24407 | 5/1999 |
| WO | WO 00/14097 | 3/2000 |
| WO | WO 01/10845 | 2/2001 |
| WO | WO 01/10848 | 2/2001 |
| WO | WO 01/19809 | 3/2001 |
| WO | WO 01/46128 | 6/2001 |
| WO | WO 01/46168 | 6/2001 |
| WO | WO 02/60895 | 8/2002 |
| WO | WO 02/66420 | 8/2002 |
| WO | WO 02/66430 | 8/2002 |
| WO | WO 02/74733 | 9/2002 |

OTHER PUBLICATIONS

Krishna, et al., "Inhibition of mast cell tryptase by inhaled APC 366 attenuates allergen–induced late–phase airway obstruction in asthma", *J. Allergy Clin. Immunol.*, Jun., 2001, pp. 1039–1045.

Rice, et al., "Dibasic Inhibitors of human mast cell tryptase. Part 2: Structure–Activity Relationships and Requirements for Potent Activity", *Bioorganic & Medicinal Chemistry Letters* 10, pp. 2361–2366 (2000).

*Primary Examiner*—Charanjit S. Aulakh
(74) *Attorney, Agent, or Firm*—Nath & Associates PLLC; Joshua B. Goldberg; Sheldon M. McGee

(57) ABSTRACT

The compounds of formula I in which M, B1, B2, R1, R2, R6, R7, K1 and K2 have the meanings as indicated in the description are novel active tryptase inhibitors.

10 Claims, No Drawings

TRYPTASE INHIBITORS

APPLICATION OF THE INVENTION

The invention relates to novel tryptase inhibitors which are used in the pharmaceutical industry for the manufacture of medicaments.

PRIOR ART

The international applications WO95/32945, WO96/09297, WO98/04537, WO99/12918, WO99/24395, WO99/24407, WO99/40073, WO99/40083, WO00/14097, WO01/10845, WO01/10848 and WO01/19809 describe low molecular weight bivalent compounds as tryptase inhibitors.

DESCRIPTION OF THE INVENTION

It has now been found that the compounds of the formula I which are described in detail below have surprising and particularly advantageous properties.

The invention relates to compounds of formula I

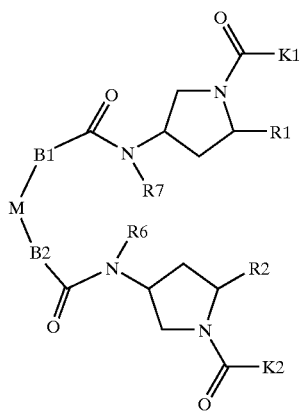

in which

M is a central structural unit selected from the following list

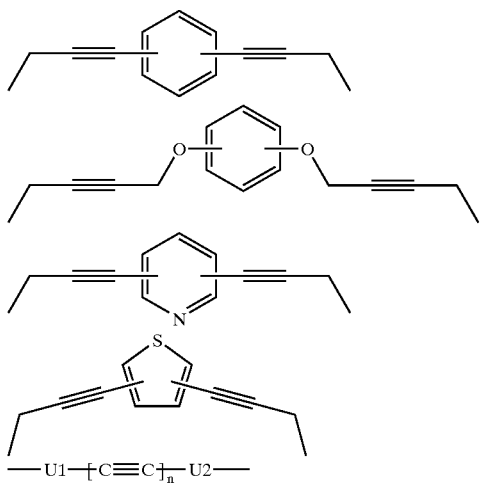

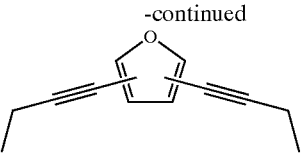

where
n is 1 or 2,
U1 and U2 are identical or different and are methylene [—$CH_2$—], ethylene [—$CH_2$—$CH_2$—], trimethylene [—$CH_2$—$CH_2$—$CH_2$—], tetramethylene [—$CH_2$—$CH_2$—$CH_2$—$CH_2$—] or isopropylidene [—$C(CH_3)_2$—],
K1 is —B3-Z1-B5-X1,
K2 is —B4-Z2-B6-X2,
B1 and B2 are identical or different and are —O—, —NH—, —O—$(CH_2)_m$—O— or —O—$(CH_2)_m$—NH—,
m is 1, 2, 3 or 4,
B3 and B4 are identical or different and are a bond or 1–2C-alkylene,
B5 and B6 are identical or different and are a bond or 1–2C-alkylene,
X1 and X2 are identical or different and are amino, aminocarbonyl, amidino or guanidino,
Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene,
R1 and R2 are identical or different and are —C(O)OR3 or —C(O)N(R4)R5, where
R3 is hydrogen, 1–4C-alkyl, 3–7C-cycloalkyl, 3–7C-cycloalkylmethyl or benzyl,
R4 and R5 are, independently of one another, hydrogen, 1–4C-alkyl, 3–7C-cycloalkyl or 3–7C-cycloalkylmethyl, or in which R4 and R5 together and with inclusion of the nitrogen atom to which they are bonded are a 1-pyrrolidinyl, 1-piperidinyl, 1-hexahydroazepinyl, 1-piperazinyl or 4-morpholinyl radical,
R6 and R7 are identical or different and are hydrogen or 1–2C-alkyl,
and the salts of these compounds.
1–4C-Alkyl stands for straight-chain or branched alkyl radicals having 1 to 4 carbon atoms. Examples which may be mentioned are the butyl, isobutyl, sec-butyl, tert-butyl, propyl, isopropyl, ethyl and methyl radicals.
3–7C-Cycloalkyl stands for cyclopropyl, cyclobutyl, cyclopentyl, cyclohexyl or cycloheptyl.
3–7C-Cycloalkylmethyl stands for a methyl radical which is substituted by one of the aforementioned 3–7C-cycloalkyl radicals. The 3–5C-cycloalkylmethyl radicals cyclopropylmethyl, cyclobutylmethyl and cyclopentylmethyl may be mentioned as preferred.
1–2C-Alkylene stands for the methylene [—$CH_2$—] or the ethylene radical [—$CH_2$—$CH_2$—].
The definition of M comprises chemical formulae such as, for example,

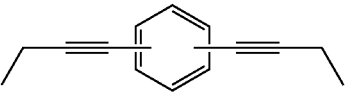

The depicted formula indicates that the two radicals —$CH_2$—C≡C— and —C≡C—$CH_2$— can be linked in any combination [(1,2)-, (1,3)- or (1,4)-] to the benzene ring.

The groups Z1 and Z2 are located by definition between the groups B3 and B5 (—B3-Z1-B5-) and B4 and B5 (—B4-Z2-B6-) respectively. Accordingly, in the divalent groups mentioned by way of example (e.g. 3,6-indolylene) the first number stands for the point of linkage to the group B3 or B4 and the second number stands for the point of linkage to the group B5 or B6.

The groups Z1 and Z2 may inter alia assume the meaning of 1,4-cyclohexylene and 1,3-cyclohexylene. The invention encompasses both compounds of the formula I in which the groups B3, B5 and B4, B6 are linked (1e,4e), (1a,4a)-, (1e,4a)-, (1a,4e)-, (1e,3e)-, (1a,3a)-, (1e,3a)- and (1a,3e)- to the cyclohexylene radical. Particular preference is given in this connection to the (1e,4e) linkage ("e" means equatorial and "a" means axial).

Various configurations are possible in the substituted pyrrolidine structural units in the compounds of the formula I. These are referred to as (2S, 4S)—, (2R, 4R)—, (2S, 4R)— and (2R, 4S)— according to the terminology of Cahn, Ingold and Prelog. The invention encompasses compounds of the formula I which may contain pyrrolidine structural units with each of these configurations. Preferred compounds of the formula I are those in which the configuration at the two pyrrolidine structural units is (2S, 4S)—.

Suitable salts for compounds of the formula I are—depending on the substitution—acid addition salts and salts with bases. Particular mention may be made of the pharmacologically suitable salts of the inorganic and organic acids normally used in pharmaceutical technology. Those suitable on the one hand are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed to prepare the salts in the equimolar ratio of amounts, or one differing therefrom—depending on whether the acid is monobasic or polybasic and depending on which salt is desired.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, once again the bases being employed to prepare the salts in the equimolar ratio of amounts or one differing therefrom.

Pharmacologically unsuitable salts which, for example, may be the initial products of the process for preparing the compounds of the Invention on the industrial scale are converted into pharmacologically suitable salts by processes known to the skilled worker.

The skilled worker is aware that the compounds of the invention and their salts when they are isolated, for example, in crystalline form may contain various amounts of solvents. The invention therefore also encompasses all solvates and, in particular, all hydrates of the compounds of the formula I, and all solvates and, in particular, all hydrates of the salts of the compounds of the formula I.

Compounds of formula I which should be emphasized are those in which M is a central structural unit selected from the following list

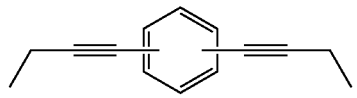

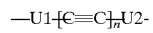

where
n is 1 or 2,
U1 and U2 are identical and are methylene [—CH$_2$—],
K1 is —B3-Z1-B5-X1,
K2 is —B4-Z2-B6-X2,
B1 and B2 are identical or different and are —O— or —O—(CH$_2$)$_m$—O—,
m is 2,
B3 and B4 are identical or different and are a bond or 1–2C-alkylene,
B5 and B6 are identical or different and are a bond or 1–2C-alkylene,
X1 and X2 are identical or different and are amino or amidino,
Z1 and Z2 are identical or different and are 1,3-phenylene, 1,4-phenylene, 1,3-cyclohexylene or 1,4-cyclohexylene,
R1 and R2 are identical or different and are —C(O)OR3 or —C(O)N(R4)R5, where
  R3 is hydrogen, 1–4C-alkyl, 3–7C-cycloalkyl, 3–7C-cycloalkylmethyl or benzyl,
  R4 and R5 are, independently of one another, hydrogen, 1–4C-alkyl, 3–7C-cycloalkyl or 3–7C-cycloalkylmethyl, or in which R4 and R5 together and with inclusion of the nitrogen atom to which they are bonded are a 1-pyrrolidinyl, 1-piperidinyl, 1-hexahydroazepinyl, 1-piperazinyl or 4-morpholinyl radical,
R6 and R7 are identical or different and are hydrogen or 1–2C-alkyl,
and the salts of these compounds.

Compounds of formula I which should be particularly emphasized are those in which
M is a central structural unit selected from the following list

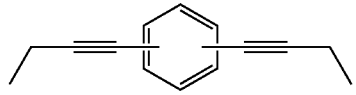

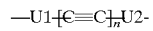

where
n is 1 or 2,
U1 and U2 are identical and are methylene [—CH$_2$—],
K1 is —B3-Z1-B5-X1,
K2 is —B4-Z2-B6-X2,
B1 and B2 are identical and are —O—,
B3 and B4 are identical and are ethylene,
B5 and B6 are identical and are methylene,
X1 and X2 are identical and are amino,
Z1 and Z2 are identical and are 1,3-phenylene or 1,4-phenylene,
R1 and R2 are identical and are —C(O)OR3,
R3 is hydrogen or 1–4C-alkyl,
R6 and R7 are identical and are hydrogen,
and the salts of these compounds.

Preferred compounds of formula I are those in which M is the following central structural unit

where
n is 1,
U1 and U2 are identical and are methylene [—CH$_2$—],
K1 is —B3-Z1-B5-X1,
K2 is —B4-Z2-B6-X2,
B1 and B2 are identical and are —O—,
B3 and B4 are identical and are ethylene,
B5 and B6 are identical and are methylene,
X1 and X2 are identical and are amino,
Z1 and Z2 are identical and are 1,3-phenylene or 1,4-phenylene,
R1 and R2 are identical and are —C(O)OR3,
R3 is hydrogen or methyl,
R6 and R7 are identical and are hydrogen,
and the salts of these compounds.

A special embodiment of the compounds according to the invention include those compounds of formula I in which M is the following central structural unit

where
n is 1,
U1 and U2 are identical and are methylene [—CH$_2$—],
K1 is —B3-Z1-B5-X1,
K2 is —B4-Z2-B6-X2,
X1 and X2 are identical and are amino,
Z1 and Z2 are identical and are 1,3-phenylene or 1,4-phenylene,
R1 and R2 are identical and are —C(O)OH or —C(O)OCH$_3$,
and the salts of these compounds.

Compounds of the formula I are composed of a large number of structural units (M, B1, B2, B3, B4, B5, B6, K1, K2, X1, X2, Z1 and Z2). Their synthesis can in principle start from any of these structural units. In the case of compounds of the formula I which have a substantially symmetrical structure it is appropriate to start the synthesis from the central structural unit M, whereas in the case of predominantly unsymmetrical compounds of the formula I it may be advantageous to start the synthesis from one of the end groups K1 or K2.

The structural units are always linked according to the same pattern which is known per se to the skilled worker.

The skilled worker is aware that either the compounds of the formula I can be synthesized structural unit by structural unit or larger fragments consisting of a plurality of individual structural units can be initially prepared and then combined to give the complete molecule.

Owing to the meanings which the individual structural units in the compounds of the formula I may assume, the compounds of the formula I comprise ether [—O—], amide [—C(O)—NH—], carbamate [—O—C(O)—NH—] or carbamide bridges [—NH—C(O)—NH—].

The way in which such bridges are prepared is known per se to the skilled worker, and suitable methods and starting compounds for preparing them are described, for example, in March, Advanced Organic Chemistry, Reactions, Mechanisms and Structure, Third Edition, 1985, John Wiley & Sons.

Ether bridges can be prepared, for example, by the Williamson method.

There is also a large number of methods known for preparing amide bridges. An example which may be mentioned here is the reaction of acid chlorides with primary or secondary amines. Reference may furthermore be made to all the methods developed for peptide chemistry.

Carbamate bridges can be prepared, for example, by reaction of chlorocarbonic esters with amines. The chlorocarbonic esters in turn can be synthesized from alcohols and phosgene. Another variant for synthesizing carbamate bridges is the addition of alcohols to isocyanates. It is possible in a similar way to the carbamate bridges to prepare carbonate bridges starting from chlorocarbonic esters by reaction with alcohols (in place of amines).

Carbamide bridges can be prepared, for example, by reaction of isocyanates with amines.

The synthesis of exemplary compounds of the formula I is depicted in the following reaction schemes. Reaction schemes 1, 2 and 3 depict the preparation of suitable starting compounds. Reaction scheme 4 depicts the preparation of example 1. Further compounds of the formula I whose preparation is not explicitly described in the reaction schemes can be prepared in an analogous way or in a way familiar to the skilled worker by use of conventional process techniques.

Reaction scheme 1:

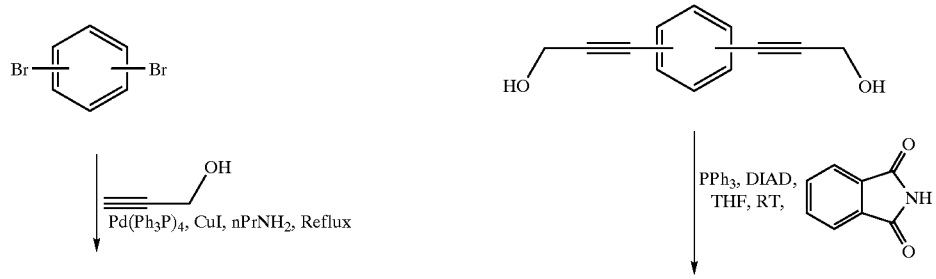

7
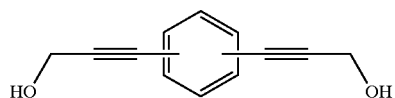
8
-continued
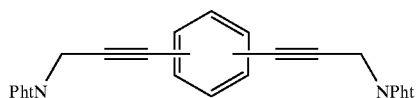
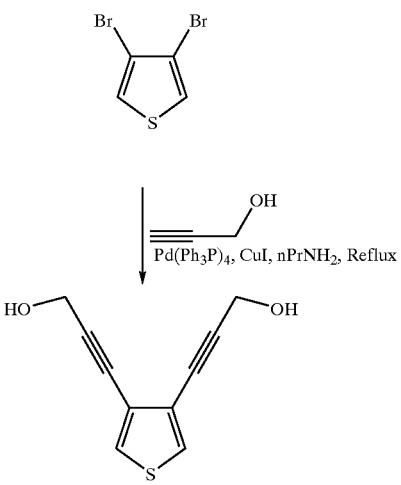
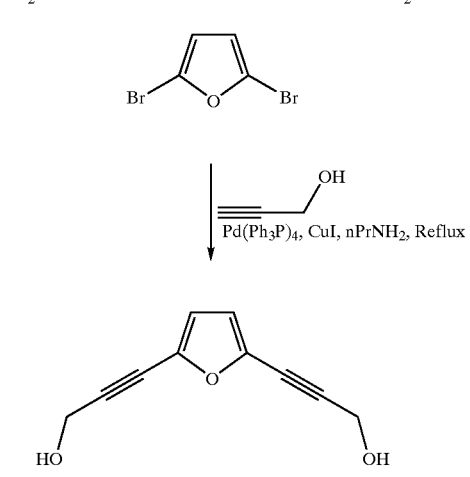
Reaction scheme 2:
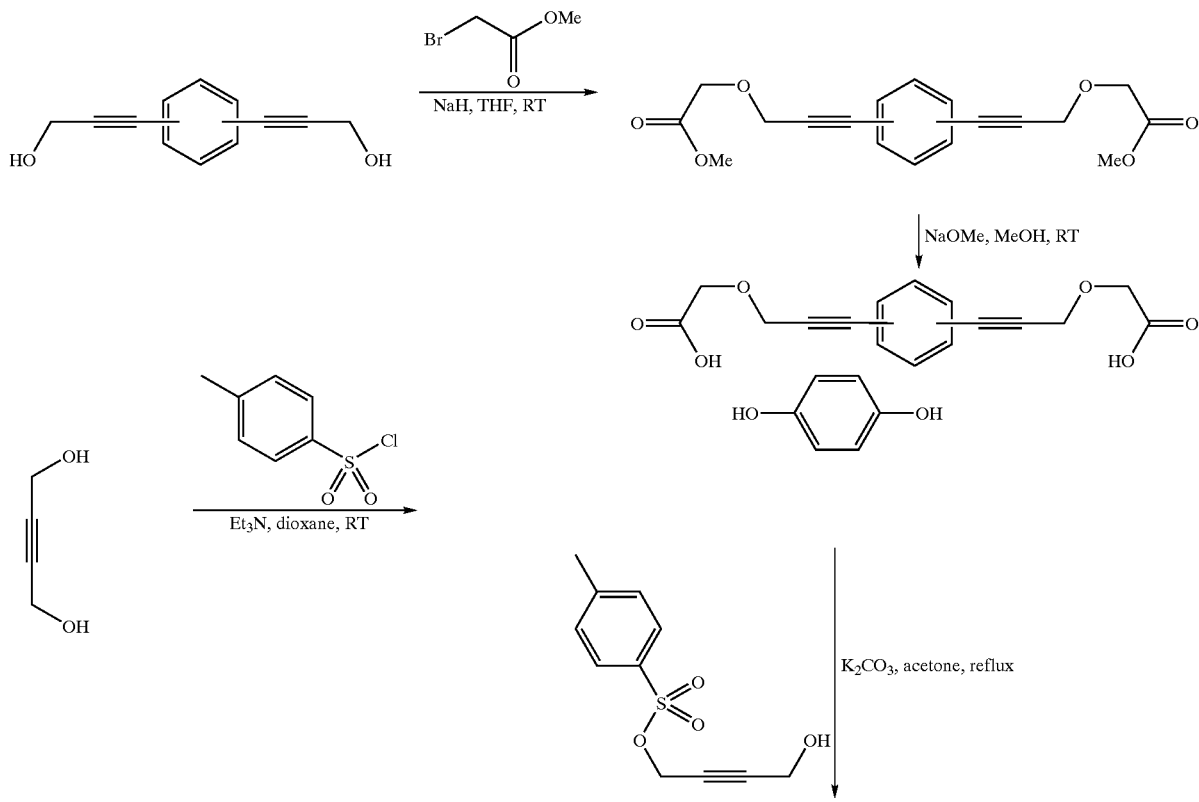

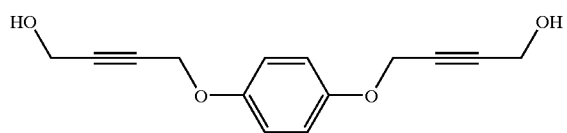
Reaction scheme 3:
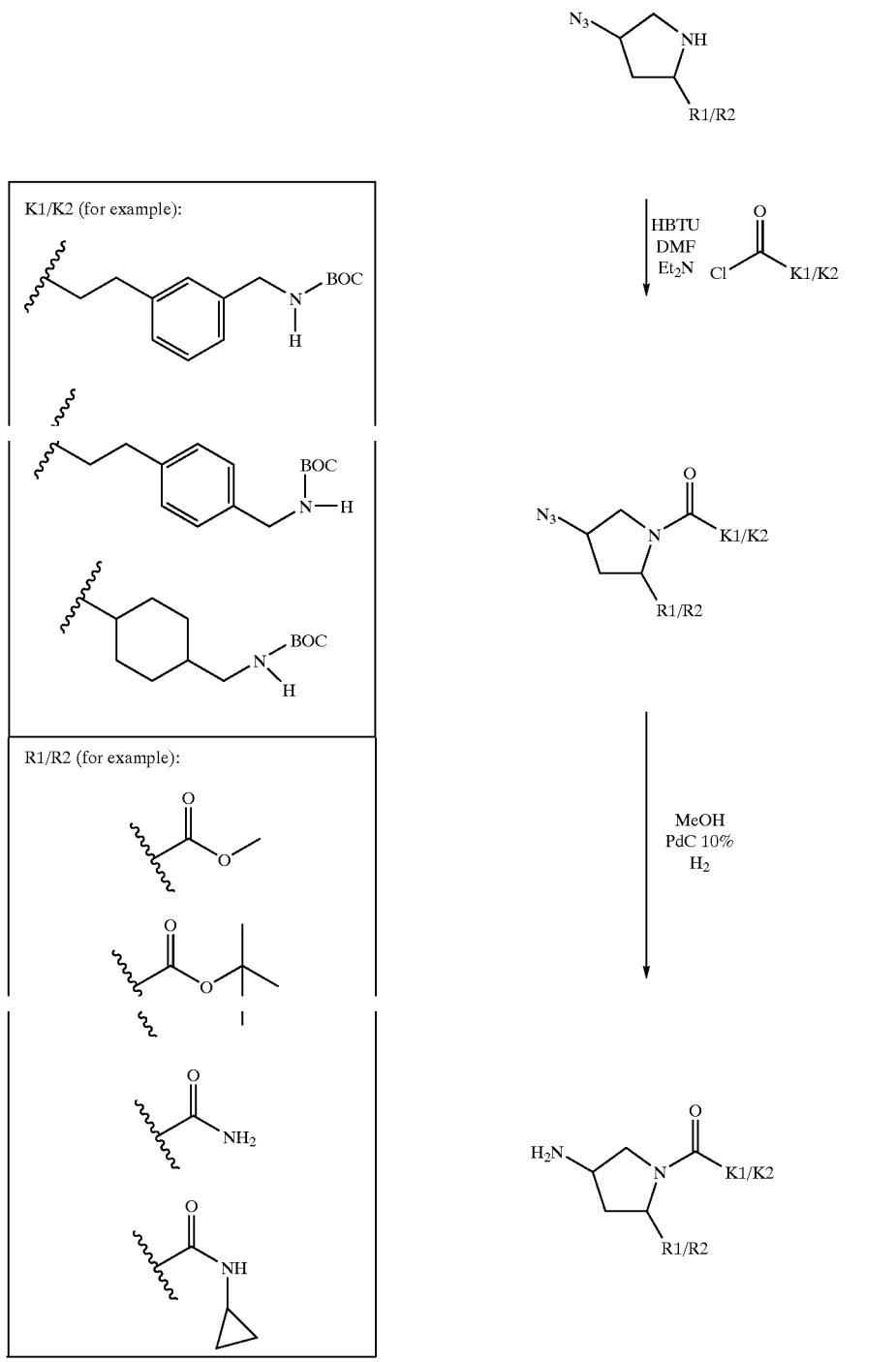

Reaction scheme 4:

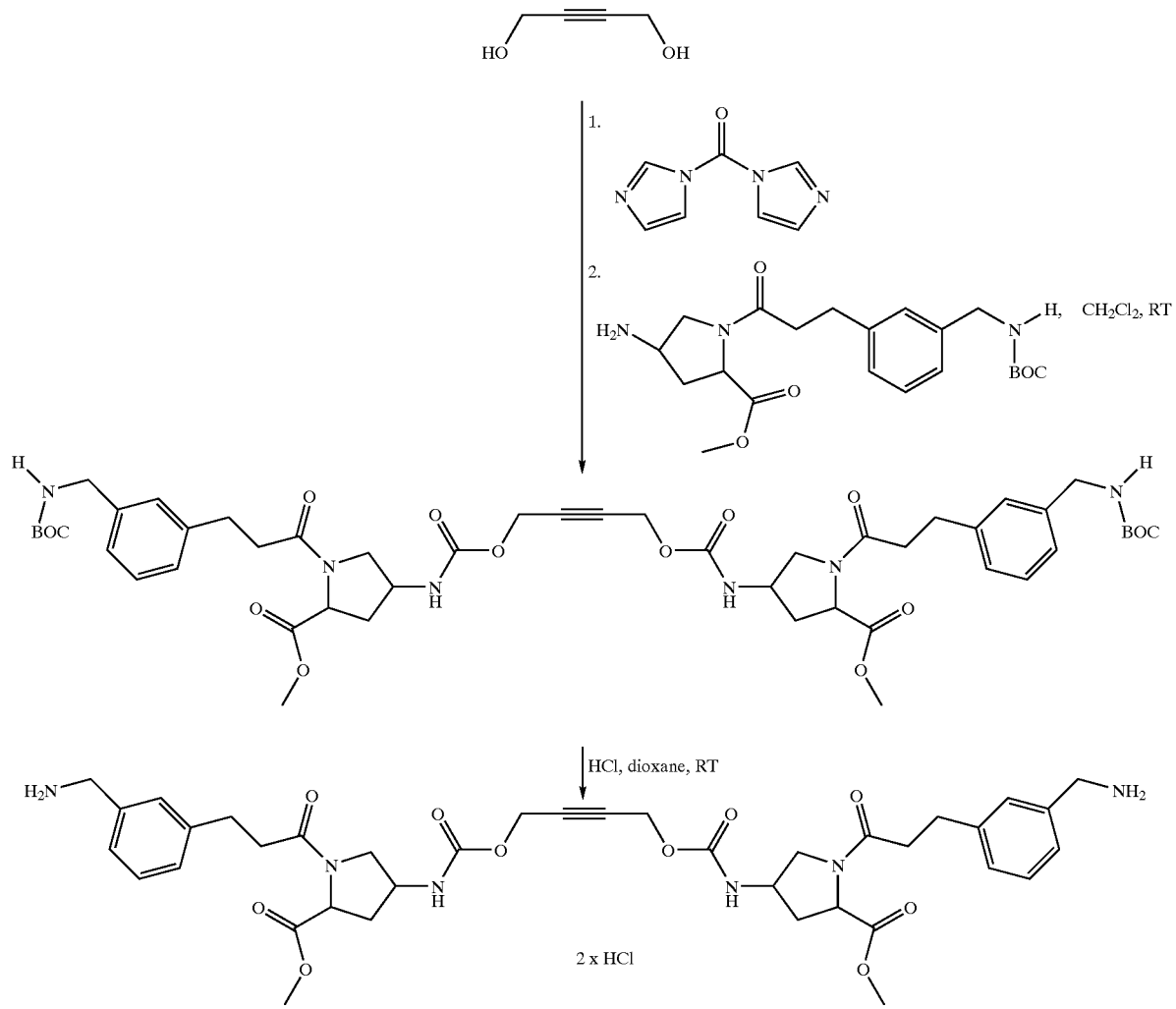

Compounds of the formula I can also be converted by derivatization into other compounds of the formula I. Thus, for example, compounds of the formula I in which R6 and R7 are hydrogen can be converted by an alkylation reaction into compounds of the formula I in which R6 and R7 are 1–2C-alkyl. The skilled worker is aware of suitable alkylation methods.

The skilled worker is additionally aware that it may be necessary where there is a plurality of reaction centers in a starting compound or intermediate to block one or more reaction centers temporarily by protective groups in order to allow a reaction to take place specifically at the desired reaction center. A detailed description of the use of a large number of useful protective groups is to be found, for example, in T. W. Greene, Protective Groups in Organic Synthesis, John Wiley & Sons, 1991.

The isolation and purification of the substances of the invention takes place in a manner known per se, for example by removing the solvent by distillation in vacuo and recrystallizing the resulting residue from a suitable solvent or subjecting it to one of the conventional purification methods such as, for example, column chromatography on suitable support material.

Salts are obtained by dissolving the free compound in a suitable solvent (e.g. a ketone such as acetone, methyl ethyl ketone or methyl isobutyl ketone, an ether such as diethyl ether, tetrahydrofuran or dioxane, a chlorinated hydrocarbon such as methylene chloride or chloroform, or a low molecular weight aliphatic alcohol such as ethanol or isopropanol) which contains the desired acid or base, or to which the desired acid or base is subsequently added. The salts are isolated by filtration, reprecipitation, precipitation using a nonsolvent for the addition salt or by evaporation of the solvent. Resulting salts can be converted by basification or acidification into the free compounds which in turn can be converted into salts. It is possible in this way to convert pharmacologically unsuitable salts into pharmacologically suitable salts.

In the following examples, the abbreviation RT stands for room temperature, h stands for hours, min. stands for minutes, HBTU stands for O-(benzotriazol-1-yl)-N,N,N',N'-tetramethyluronium hexafluorophosphate, calc. stands for calculated and fd stands for found.

The invention preferably relates to the compounds mentioned by way of example and their salts.

EXAMPLES

Final Compounds:

General Method

A saturated solution of HCl in dioxane (21 ml) is added to a solution of the particular Boc-protected bivalent compound (A1-A3, 0.1 mmol) in dioxane (21 ml), and the mixture is stirred at RT for 1–8 h. The reaction mixture is then diluted with diethyl ether (10 ml) and the resulting precipitate is filtered off and washed with diethyl ether (3×5 ml). Drying in vacuo results in the title compounds (final compounds 1–3) as colorless solids.

1. 1,4-Bis-{N-[3-(3-aminomethylphenylproplonyl)-2-methoxycarbonylpyrrolidin-4-yl]aminocarbonyloxy}-2-butyne dihydrochloride

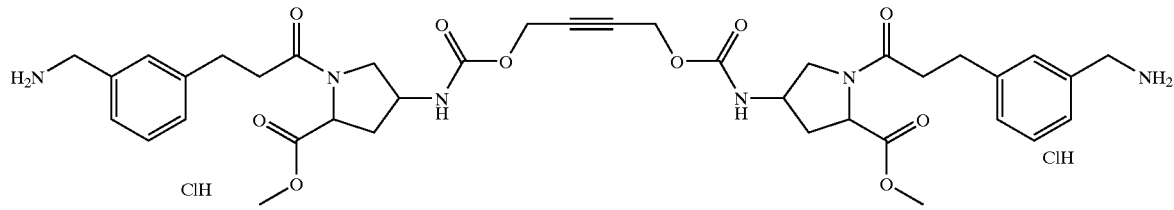

MS: calc.: $C_{38}H_{48}N_8O_{10}$ (748.9), fd: [MH$^+$] 749.4

2. 1,4-Bis-{N-[3-(4-aminomethylphenylproplonyl)-2-methoxycarbonylpyrrolidin-4-yl]aminocarbonyloxy}-2-butyne dihydrochloride

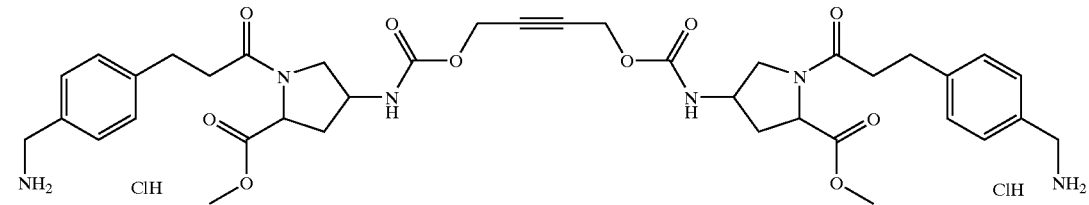

MS: calc.: $C_{38}H_{48}N_8O_{10}$ (748.9), fd: [MH$^+$] 749.4

3. 1,4-Bis-{N-[3-(4-aminomethylphenylproplonyl)-2-carboxypyrrolidin-4-yl]aminocarbonyloxy}-2-butyne dihydrochloride

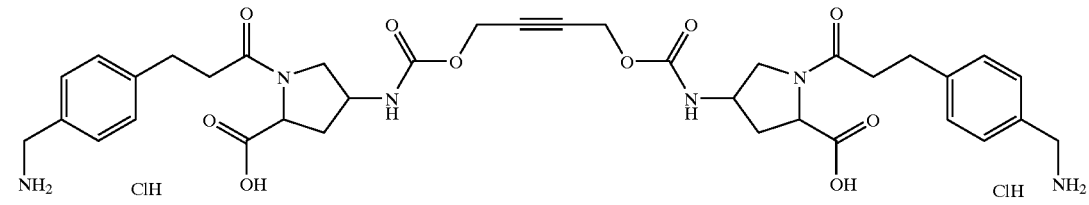

MS: $C_{36}H_{44}N_6O_{10}$ (720.8), fd: [MH$^+$] 721.6

Starting Compounds:

A1. 1,4-Bis-{N-[3-(3-tert-butyloxycarbonylaminomethylphenylproplonyl)-2-methoxycarbonylpyrrolidin-4-yl]aminocarbonyloxy}-2-butyne N,N'-Carbonyldiimidazole (0.75 g, 3.0 mmol) is added to a solution of 2-butyne-1,4-diol (0.13 g, 1.50 mmol) in absolute $CH_2Cl_2$ (4 ml) and the mixture is stirred at RT for 2 h. The reaction solution is diluted with $CH_2Cl_2$ (4 ml) and extracted with a half-saturated aqueous NaCl solution (10 ml). The organic phase is dried over $MgSO_4$, filtered and concentrated in vacuo. The resulting residue is taken up in absolute $CH_2Cl_2$ (4 ml) and, after addition of 4-amino-1-[3-(3-tert-butyloxycarbonylaminomethylphenyl)propionyl]proline methyl ester (starting compound A9, 1.2 g, 3.0 mmol), stirred at RT overnight. The reaction solution is then diluted with ethyl acetate (15 ml) and extracted with a half-saturated aqueous $NH_4Cl$ solution (20 ml). The organic phase is dried over $MgSO_4$, filtered and concentrated in vacuo. Further purification takes place by chromatography [Tol/Ac (7:3)] on a silica gel column. The title compound (0.42 g) is obtained as a colorless amorphous residue. TLC, silica gel (glass plates), [toluene/acetone (7:3)], $R_f$=0.17.

MS: calc.: $C_{48}H_{64}N_6O_{14}$ (948.0), fd: [MH$^+$] 949.0, [MNa$^+$] 971.5

A2. 1,4-Bis-{N-[3-(4-tert-butyloxycarbonylaminomethylphenylproplonyl)-2-methoxycarbonylpyrrolidin-4-yl]aminocarbonyloxy}-2-butyne N,N'-Carbonyldiimidazole (0.75 g, 3.0 mmol) is added to a solution of 2-butyne-1,4-diol (0.13 g, 1.50 mmol) in absolute $CH_2Cl_2$ (5 ml) and the mixture is stirred at RT for 2 h. The reaction solution is diluted with $CH_2Cl_2$ (5 ml) and extracted with a half-saturated aqueous NaCl solution (10 ml). The organic phase is dried over $MgSO_4$, filtered and concentrated in vacuo. The resulting residue is taken up in absolute $CH_2Cl_2$ (5 ml) and, after addition of 4-amino-1-

[3-(4-tert-butyloxycarbonylaminomethylphenyl)propionyl] proline methyl ester (starting compound A4, 1.2 g, 3.0 mmol), stirred at RT overnight. The reaction solution is then diluted with ethyl acetate (15 ml) and extracted with a half-saturated aqueous NH$_4$Cl solution (20 ml). The organic phase is dried over MgSO$_4$, filtered and concentrated in vacuo. Further purification takes place by chromatography [Tol/Ac (7:3)] on a silica gel column. The title compound (1.0 g) Is obtained as a colorless amorphous residue. TLC, silica gel (glass plates), [toluene/acetone (7:3)], R$_f$=0.15.

MS: calc.: C$_{48}$H$_{84}$N$_6$O$_{14}$ (948.0), fd: [MH$^+$] 949.1, [MNa$^+$] 971.5

A3. 1,4-Bis-{N-[3-(4-tert-butyloxycarbonylaminomethylphenylpropionyl)-2-carboxypyrrolidin-4-yl]aminocarbonyloxy}-2-butyne A 5 N aqueous NaOH solution (2 ml) is added dropwise to a suspension of 1,4-bis-{N-[3-(4-tert-butyloxycarbonylaminomethylphenylpropionyl)-2-methoxycarbonylpyrrolidin-4-yl]aminocarbonyloxy}2-butyne (A2, 0.6 g, 0.63 mmol) in ethanol (6 ml), and the mixture is stirred at RT for 1 h. The reaction mixture is adjusted to pH 3 with a 20% aqueous KHSO$_3$ solution and extracted with CH$_2$Cl$_2$ (50 ml). The organic phase is then dried over MgSO$_4$, filtered and concentrated in vacuo. The title compound (0.15 g) is obtained as a colorless solid. TLC, silica gel (glass plates), [Tol/Ac (6:4)], R$_f$=0.1.

A4. 4-Amino-1-[3-(4-tert-butyloxycarbonylaminomethylphenyl)propionyl] proline methyl ester 6.27 g (14.5 mmol) of 4-azido-1-[3-(4-tert-butyloxycarbonylaminomethylphenyl)propionyl]proline methyl ester (starting compound A5) are dissolved in 200 ml of methanol and, after addition of 0.6 g of Pd/C (10%), hydrogenated. After the reaction is complete, the catalyst is filtered off with suction and the filtrate is concentrated in vacuo. Drying under high vacuum results in 5.47 g of the title compound as a colorless solidified foam. The mass spectrum shows the molecular peak MH$^+$ at 406 Da.

A5. 4-Azido-1-[3-(4-tert-butyloxycarbonylaminomethylphenyl)propionyl] proline methyl ester 2.70 g (9.5 mmol) of 3-(4-tert-butyloxycarbonylaminomethylphenyl)propionic acid (starting compound A6) are dissolved in 40 ml of DMF, and 2.7 ml of triethylamine are added. After stirring for 5 min., 3.63 g of HBTU are added and, after a further 5 min., 2 g of (2S,4S)-4-azidoproline methyl ester hydrochloride. Stirring at RT overnight is followed by addition of ethyl acetate and water and separation of the phases. The organic phase is washed once each with 1N sodium hydroxide solution, 1N hydrochloric acid solution, saturated sodium bicarbonate solution and saturated brine. Drying over magnesium sulfate is followed by concentration and drying under high vacuum. 4.1 g of the title compound are obtained as a pale orange oil. The mass spectrum shows the molecular peak MNH$_4^+$ at 449 Da.

A6. 3-(4-tert-Butyloxycarbonylaminomethylphenyl) propionic acid 4.65 g of methyl 3-(4-aminomethylphenyl)propionate hydrochloride (starting compound A7) are dissolved in 20 ml of dichloromethane and, while stirring at 0° C., 6.17 ml of triethylamine and a solution of 4.62 g of di-tert-butyl dicarbonate in 10 ml of dichloromethane are successively added. The reaction solution is stirred at 0° C. for 1 h and at RT for a further 3 h and then washed twice with 0.1N hydrochloric acid solution and then with sodium bicarbonate solution and water, and dried over magnesium sulfate. Filtration is followed by concentration in vacuo, and the residue (5.6 g) is dissolved in 50 ml of tetrahydrofuran, and 13.4 ml of 2N sodium hydroxide solution are added. After stirring at RT overnight, 6.7 ml of 4N hydrochloric acid solution are used to neutralize, and the organic solvent is removed by distillation in vacuo. The resulting colorless precipitate is filtered off with suction, washed with water and dried under high vacuum. 4.65 g of the title compound are obtained, and the mass spectrum thereof shows the molecular peak MNH$_4^+$ at 297 Da.

A7. Methyl 3-(4-aminomethylphenyl)propionate hydrochloride 5.6 g of methyl 4-(hydroxyiminomethyl)cinnamate (starting compound A8) are dissolved in a mixture of 170 ml of methanol and 50 ml of acetic acid and hydrogenated over 0.5 g of palladium/carbon (10%) for 4 h. The catalyst is filtered off and the filtrate is concentrated in vacuo. The residue is stirred with ether and then a solution of hydrogen chloride in ether is added. The resulting precipitate is filtered off with suction, washed with ether and dried in vacuo. 4.65 g of the title compound are obtained. The mass spectrum shows the molecular peak MH$^+$ at 194 Da.

A8. Methyl 4-(hydroxyiminomethyl)cinnamate 4.0 g of methyl 4-fornylcinnamate are dissolved in 40 ml of methanol and 1.6 g of hydroxylamine hydrochloride and 1.9 g of sodium acetate are successively added. The mixture is stirred overnight and then diluted with 300 ml of water, and the resulting precipitate is filtered off with suction. Drying under high vacuum and recrystallization from ethyl acetate/petroleum ether result in 3.56 g of the title compound. The mass spectrum shows the molecular peak MH$^+$ at 206 Da.

A9. 4-Amino-1-[3-(3-tert-butyloxycarbonylaminomethylphenyl)propionyl] proline methyl ester 4.7 g (10.9 mmol) of 4-azido-1-[3-(3-tert-butyloxycarbonylaminomethylphenyl)propionyl]proline methyl ester (starting compound A10) are dissolved in 70 ml of methanol and, after addition of 0.5 g of Pd/C (10%), hydrogenated. After the reaction is complete, the catalyst is filtered off with suction and the filtrate is concentrated in vacuo. Drying under high vacuum results in 3.8 g of the title compound as a colorless solidified foam. The mass spectrum shows the molecular peak MH$^+$ at 406 Da.

A10. 4-Azido-1-[3-(3-tert-butyloxycarbonylaminomethylphenyl)propionyl] proline methyl ester 1.61 g (5.7 mmol) of 3-(3-tert-butyloxycarbonylaminomethylphenyl)propionic acid (starting compound A11) are dissolved in 14 ml of CH$_2$Cl$_2$, and 2.1 ml of DIPEA are added. After stirring for 5 min., 2.2 g (5.7 mmol) of HBTU are added and, after a further 5 min., 1.0 g (4.8 mmol) of (2S,4S)-4-azidoproline methyl ester hydrochloride. After stirring at RT overnight, ethyl acetate and water are added and the phases are separated. The organic phase is washed once each with 1N sodium hydroxide solution, 1N hydrochloric acid solution, saturated sodium bicarbonate solution and saturated brine. Drying over magnesium sulfate is followed by concentration and drying under high vacuum. Further purification takes place by chromatography [Tol/Ac (8:2)] on a silica gel column. The title compound (1.5 g) is obtained as a colorless oil. TLC, silica gel (glass plates), [toluene/acetone (8:2)], $R_f$=0.31. The mass spectrum shows the molecular peak $MNH_4^+$ at 449 Da.

A11. 3-(3-tert-Butyloxycarbonylaminomethylphenyl)propionic acid 19.46 g of methyl 3-(3-aminomethylphenyl)propionate hydrochloride (starting compound A12) are dissolved in 200 ml of dichloromethane and, while stirring at 0° C., 27 ml of triethylamine and a solution of 16.8 g of di-tert-butyl dicarbonate in 10 ml of dichloromethane are successively added. After stirring at 0° C. for 1 h and at RT for a further 3 h, the reaction solution is washed twice with 0.1N hydrochloric acid solution and then with sodium bicarbonate solution and water, and dried over magnesium sulfate. Filtration is followed by concentration in vacuo, and the residue (13.5 g) is dissolved in 188 ml of tetrahydrofuran, and 38 ml of 2N sodium hydroxide solution are added. After stirring at RT overnight, 4N hydrochloric acid is used to neutralize, and the organic solvent is removed by distillation in vacuo. The resulting colorless precipitate Is filtered off with suction, washed with water and dried under high vacuum. 12.8 g of the title compound are obtained, and its mass spectrum shows the molecular peak $MNH_4^+$ at 297 Da.

A12. Methyl 3-(3-aminomethylphenyl)propionate hydrochloride 12.5 g of methyl (E)-3-(3-cyanophenyl)acrylate (starting compound A13) are dissolved in a mixture of 130 ml of methanol and 8 ml of acetic acid and hydrogenated over 1.3 g of palladium/carbon (10%) for 4 h. The catalyst is filtered off and the filtrate is concentrated in vacuo. The residue is stirred with ether and then a solution of hydrogen chloride in ether is added. The resulting precipitate is filtered off with suction, washed with ether and dried in vacuo. 19.5 g of the title compound are obtained. The mass spectrum shows the molecular peak $MH^+$ at 194 Da.

A13. Methyl (E)-3-(3-cyanophenyl)acrylate 7.31 ml (74.5 mmol) of methyl acrylate, 13.6 g (74.5 mmol) of 3-bromobenzonitrile and 6.6 g (74.5 mmol) of sodium acetate are suspended in 100 ml of DMF and heated at 120° C. for 30 min until a clear solution has formed. Then a solution of 4.0 g of palladium acetate and 21.0 g of tri-p-tolylphosphine in 5 ml of DMF is added dropwise to the reaction solution, and the mixture is stirred at 120° C. for 2 h. The reaction solution is then diluted with 500 ml of water, and the resulting precipitate is filtered off with suction. Drying under high vacuum and recrystallization from ethyl acetate/petroleum ether result in 12.6 g of the title compound. The mass spectrum shows the molecular peak $MH^+$ at 187.7 Da.

INDUSTRIAL APPLICATION

The compounds of the invention have, as tryptase inhibitors, valuable pharmacological properties which make them immensely utilizable. Human tryptase is a serine protease which is the predominant protein present in human mast cells. Tryptase comprises eight closely related enzymes (α1, α2, β1a, β1b, β2, β3, mMCP-7-like-1, mMCP-7-like-2; 85 to 99% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815; Pallaoro et al., J. Biol. Chem. 274 (1999) 3355–3362). However, only β-tryptases (Schwartz et al., J. Clin. Invest. 96 (1995) 2702–2710; Sakai et al., J. Clin. Invest. 97 (1996) 988–995) undergo intracellular activation and are stored in catalytically active form in secretory granules. Tryptase has some special properties by comparison with other known serine proteases such as, for example, trypsin or chymotrypsin (Schwartz et al., Methods Enzymol. 244, (1994), 88–100; G. H. Caughey, "Mast cell proteases in immunology and biology", Marcel Dekker, Inc., New York, 1995). Tryptase from human tissue has a non-covalently linked tetrameric structure which must be stabilized by heparin or other proteoglycans in order to have proteolytic activity. Tryptase is released together with other inflammatory mediators such as, for example, histamine and proteoglycans when human mast cells are activated. It is therefore assumed that tryptase is involved in a number of disorders, in particular in allergic and inflammatory disorders, on the one hand because of the significance of mast cells in such disorders, and on the other hand because an increased tryptase content has been found in a number of such disorders. Thus, tryptase is thought to be associated inter alia with the following disorders: acute and chronic (especially inflammatory and allergen-induced) airway disorders of various etiologies (e.g. bronchitis, allergic bronchitis, bronchial asthma, COPD); interstitial pulmonary disorders; disorders based on allergic reactions with the upper airways (pharynx, nose) and the adjacent regions (e.g. paranasal sinuses, conjunctivae), such as, for example, allergic conjunctivitis and allergic rhinitis; arthritic diseases (e.g. rheumatoid arthritis); autoimmune diseases such as multiple sclerosis; also neurogenic inflammations, arteriosclerosis and cancer; additionally periodontitis, anaphylaxis, interstitial cystitis, dermatitis, psoriasis, scleroderma/systemic sclerosis, inflammatory bowel disorders (Crohn's disease, ulcerative colitis) and others. Tryptase appears In particular to be directly associated with the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, sections 3.3.1–3.3.23).

The invention further relates to the compounds of the invention for use in the treatment and/or prophylaxis of disorders, especially of the disorders mentioned.

The invention likewise relates to the use of the compounds of the invention for producing medicaments employed for the treatment and/or prophylaxis of the disorders mentioned.

The invention further relates to medicaments which comprise one or more of the compounds of the invention for the treatment and/or prophylaxis of the disorders mentioned.

The medicaments are produced by processes known per se and familiar to the skilled worker. The compounds of the invention (=active ingredients) are employed as medicaments either as such or, preferably, In combination with suitable pharmaceutical excipients, e.g. in the form of tablets, coated tablets, capsules, suppositories, plasters, emulsions, suspensions, gels or solutions, with the content of active ingredient advantageously being between 0.1 and 95%.

The skilled worker is aware of the excipients which are suitable for the desired pharmaceutical formulations on the basis of his expert knowledge. Besides solvents, gel formers, ointment bases and other active ingredient carriers it is possible to use, for example, antioxidants, dispersants, emulsifiers, preservatives, solubilizers or permeation promoters.

For the treatment of disorders of the respiratory tract, the compounds of the invention are preferably also administered by inhalation, preferably in the form of an aerosol, with the aerosol particles of a solid, liquid or mixed composition having a diameter of from 0.5 to 10 μm, advantageously from 2 to 6 μm.

The aerosols can be generated for example by pressure-operated nozzle nebulizers or ultrasonic nebulizers, but advantageously by metered aerosols operated by propellant gas or propellant gas-free use of micronized active ingredients from inhalation capsules.

Depending on the inhalation system used, the dosage forms comprise besides the active ingredients also the necessary excipients such as, for example, propellant gases (e.g. Frigen in the case of metered aerosols), surface-active substances, emulsifiers, stabilizers, preservatives, aromatic substances, fillers (e.g. lactose in the case of powder inhalers) or, where appropriate, further active ingredients.

For inhalation purposes there are a large number of available appliances with which aerosols of optimal particle size can be generated and administered using an inhalation technique which is as appropriate for the patient as possible. Besides the use of attachments (spacers, expanders) and pear-shaped containers (e.g. Nebulator®, Volumatic®) and automatic actuators (Autohaler®) for metered aerosols, there are, especially for powder inhalers, a number of available technical solutions (e.g. Diskhaler®, Rotadisk®, Turbohaler® or the inhaler described in European patent application EP 0 504 321) with which optimal administration of active ingredient can be achieved.

For the treatment of dermatoses, the compounds of the invention are used in particular in the form of medicaments which are suitable for topical application. The medicaments are produced by mixing the compounds of the invention (=active ingredients) preferably with suitable pharmaceutical excipients and further processing to suitable pharmaceutical formulations. Examples of suitable pharmaceutical formulations which may be mentioned are dusting powders, emulsions, suspensions, sprays, oils, ointments, fatty ointments, creams, pastes, gels or solutions.

The medicaments of the invention are produced by processes known per se. The dosage of the active ingredients on systemic therapy (oral or i.v.) is between 0.1 and 10 mg per kilogram and day.

Biological Investigations

The documented pathophysiological effects of mast cell tryptase are brought about directly by the enzymatic activity of the protease. Accordingly, they are reduced or blocked by inhibitors which inhibit the enzymatic activity of tryptase. A suitable measure of the affinity of a reversible inhibitor for the target protease is the equilibrium dissociation constant $K_i$ of the enzyme/inhibitor complex. This value of $K_i$ can be determined via the influence of the inhibitor on the tryptase-induced cleavage of a chromogenic peptide-p-nitroanilide substrate or of a fluorogenic peptide-aminomethylcoumarin substrate.

Methods

The dissociation constants for the tryptase/inhibitor complexes are determined under equilibrium conditions in accordance with the general proposals of Bieth (Bieth J. G., Pathophysiological Interpretation of kinetic constants of protease inhibitors, Bull. Europ. Physiopath. Resp. 16:183–195, 1980) and the methods of Sommerhoff et al. (Sommerhoff C. P. et al., A Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is prepared pure from lung tissue or is prepared by recombination; the specific activity of the protease which has been determined by titration is normally more than 85% of the theoretical value. Constant amounts of the tryptase are incubated in the presence of heparin (0.1–50 μg/ml) to stabilize the protease with increasing amounts of the inhibitors. After equilibrium has been reached between the reactants, the remaining enzymatic activity is determined after addition of the peptide-p-nitroanilide substrate tos-Gly-Pro-Arg-pNA, whose cleavage is followed at 405 nm for 3 min. Alternatively, the remaining enzymatic activity can also be determined using fluorogenic substrates. The apparent dissociation constants $K_{iapp}$ (i.e. in the presence of substrate) are then found by nonlinear regression by fitting the enzyme rates to the general equation for reversible inhibitors (Morrison J. F, Kinetics of the reversible inhibition of enzyme catalysed reactions by tight-binding inhibitors, Biochim. Biophys. Acta 185, 269–286, 1969):

$$V_1/V_0 = 1 - \{E_t + I_t + K_{iapp} - [(E_t + I_t + K_{iapp})^2 - 4E_t I_t]^{1/2}\}/2E_t$$

In this, $V_1$ and $V_0$ are the rates respectively in the presence and absence of the inhibitor and $E_t$ and $I_t$ are the concentrations of tryptase and of the inhibitor.

The apparent dissociation constants found for the compounds of the invention are evident from the following table A, in which the numbers of the compounds correspond to the numbers of the compounds in the examples [$pK_{iapp}$ = $-\log K_{iapp}$ (mol/l)].

TABLE A

| Inhibition of human tryptase | |
| --- | --- |
| Compound | $pK_{iapp}$ |
| 1 | 8.35 |

What is claimed is:
1. A compound of formula I

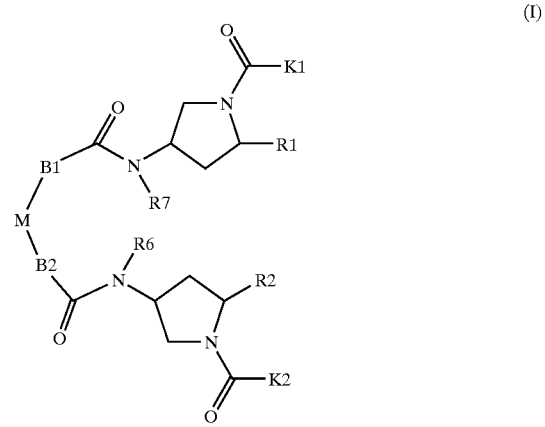

in which
M is a central structural unit selected from the following list

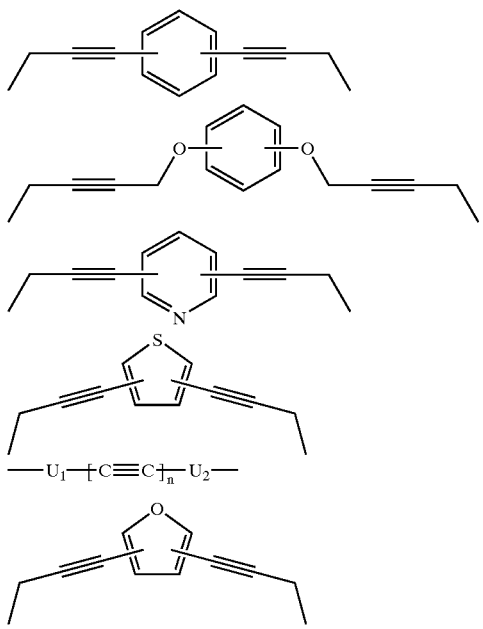

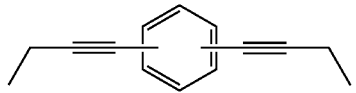

where
n is 1 or 2,
U1 and U2 are identical or different and are methylene [—CH$_2$—], ethylene [—CH$_2$—CH$_2$—], trimethylene [—CH$_2$—CH$_2$—CH$_2$—], tetramethylene [—CH$_2$—CH$_2$—CH$_2$—CH$_2$—] or isopropylidene [—C(CH$_3$)$_2$—],
K1 is —B3-Z1-B5-X1,
K2 is —B4-Z2-B6-X2,
B1 and B2 are identical or different and are —O—, —NH—, —O—(CH$_2$)$_m$—O—, or —O—(CH$_2$)$_m$—NH—,
m is 1, 2, 3 or 4,
B3 and B4 are identical or different and are a bond or 1–2C-alkylene,
B5 and B6 are identical or different and are a bond or 1–2C-alkylene,
X1 and X2 are identical or different and are amino, aminocarbonyl, amidino or guanidino,
Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene,
R1 and R2 are identical or different and are —C(O)OR3 or —C(O)N(R4)R5,
where
R3 is hydrogen, 1–4C-alkyl, 3–7C-cycloalkyl, 3–7C-cycloalkylmethyl or benzyl,
R4 and R5 are, independently of one another, hydrogen, 1–4C-alkyl, 3–7C-cycloalkyl or 3–7C-cycloalkylmethyl, or in which R4 and R5 together and with inclusion of the nitrogen atom to which they are bonded are a 1-pyrrolidinyl, 1-piperadinyl, 1-hexahydroazepinyl, 1-piperazinyl or 4-morpholinyl radical,
R6 and R7 are identical or different and are hydrogen or 1–2C-alkyl,
or a salt, hydrate, hydrate of a salt, solvate or solvate of a salt thereof.

2. A compound of formula I as claimed in claim 1, in which
M is a central structural unit selected from the following list

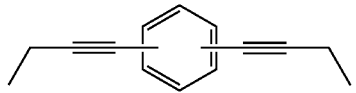

where
n is 1 or 2,
U1 and U2 are identical and are methylene [—CH$_2$—],
K1 is —B3-Z1-B5-X1,
K2 is —B4-Z2-B6-X2,
B1 and B2 are identical or different and are —O—, or —O—(CH$_2$)$_m$—O—,
m is 2,
B3 and B4 are identical or different and are a bond or 1–2C-alkylene,
B5 and B6 are identical or different and are a bond or 1–2C-alkylene,
X1 and X2 are identical or different and are amino or amidino,
Z1 and Z2 are identical or different and are 1,3-phenylene, 1,4-phenylene, 1,3-cyclohexylene or 1,4-cyclohexylene,
R1 and R2 are identical or different and are —C(O)OR3 or —C(O)N(R4)R5,
where
R3 is hydrogen, 1–40-alkyl, 3–7C-cycloalkyl, 3–7C-cycloalkylmethyl or benzyl,
R4 and R5 are, independently of one another, hydrogen, 1–4C-alkyl, 3–7C-cycloalkyl or 3–7C-cycloalkylmethyl, or in which R4 and R5 together and with inclusion of the nitrogen atom to which they are bonded are a 1-pyrrolidinyl, 1-piperadinyl, 1-hexahydroazepinyl, 1-piperazinyl or 4-morpholinyl radical,
R6 and R7 are identical or different and are hydrogen or 1–2C-alkyl,
or a salt, hydrate, hydrate of a salt, solvate or solvate of a salt thereof.

3. A compound of formula I as claimed in claim 1, in which
M is a central structural unit selected from the following list

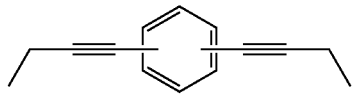

where
n is 1 or 2,
U1 and U2 are identical and are methylene [—CH$_2$—],
K1 is —B3-Z1-B5-X1,
K2 is —B4-Z2-B6-X2,
B1 and B2 are identical and are —O—,
B3 and B4 are identical and are ethylene,
B5 and B6 are identical and are methylene, X1 and X2 are identical and are amino,
Z1 and Z2 are identical and are 1,3-phenylene or 1,4-phenylene,
R1 and R2 are identical and are —C(O)OR3,
R3 is hydrogen or 1–4C-alkyl,
R6 and R7 are identical and are hydrogen,
or a salt, hydrate, hydrate of a salt, solvate or solvate of a salt thereof.

4. A compound of formula I as claimed in claim 1, in which

M is the following central structural unit

where
n is 1,
U1 and U2 are identical and are methylene [—CH$_2$—],
K1 is —B3-Z1-B5-X1,
K2 is —B4-Z2-B6-X2,
B1 and B2 are identical and are —O—,
B3 and B4 are identical and are ethylene,
B5 and B6 are identical and are methylene,
X1 and X2 are identical and are amino,
Z1 and Z2 are identical and are 1,3-phenylene or 1,4-phenylene,
R1 and R2 are identical and are —C(O)OR3,
R3 is hydrogen or methyl,
R6 and R7 are identical and are hydrogen,
or a salt, hydrate, hydrate of a salt, solvate or solvate of a salt thereof.

5. A compound of formula I as claimed in claim 1, in which

M is the following central structural unit

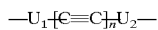

where
n is 1,
U1 and U2 are identical and are methylene [—CH$_2$—],
K1 is —B3-Z1-B5-X1,
K2 is —B4-Z2-B6-X2,
X1 and X2 are identical and are amino,
Z1 and Z2 are identical and are 1,3-phenylene or 1,4-phenylene,
R1 and R2 are identical and are —C(O)OR3,
R3 is hydrogen or methyl,
or a salt, hydrate, hydrate of a salt, solvate or solvate of a salt thereof.

6. A pharmaceutical composition comprising one or more compounds of formula I as claimed in claim 1 or a pharmaceutically acceptable salt, hydrate, hydrate of a salt, solvate or solvate of a salt thereof, together with a pharmaceutical excipient.

7. A method of treating a disease or disorder in a patient comprising administering to a patient in need thereof a therapeutically effective amount of one or more compounds of formula I as claimed in claim 1 or a pharmaceutically acceptable salt, hydrate, hydrate of a salt, solvate or solvate of a salt thereof, wherein the disease or disorder is selected from the group consisting of asthma, allergic conjunctivitis, allergic rhinitis, psoriasis, sclerodermatitis and ulcerative colitis.

8. A method of treating an airway disorder in a patient comprising administering to a patient in need thereof a therapeutically effective amount of one or more compounds of formula I as claimed in claim 1 or a pharmaceutically acceptable salt, hydrate, hydrate of a salt, solvate or solvate of a salt thereof, wherein the airway disorder is selected from the group consisting of asthma and allergic rhinitis.

9. A compound of formula I as claimed in claim 2, in which

M is the following central structural unit

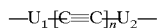

where
n is 1,
U1 and U2 are identical and are methylene [—CH$_2$—],
K1 is —B3-Z1-B5-X1,
K2 is —B4-Z2-B6-X2,
X1 and X2 are identical and are amino,
Z1 and Z2 are identical and are 1,3-phenylene or 1,4-phenylene,
R1 and R2 are identical and are —C(O)OR3,
R3 is hydrogen or methyl,
or a salt, hydrate, hydrate of a salt, solvate or solvate of a salt thereof.

10. A compound of formula I as claimed in claim 3, in which

M is the following central structural unit

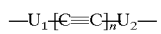

where
n is 1,
U1 and U2 are identical and are methylene [—CH$_2$—],
K1 is —B3-Z1-B5-X1,
K2 is —B4-Z2-B6-X2,
X1 and X2 are identical and are amino,
Z1 and Z2 are identical and are 1,3-phenylene or 1,4-phenylene,
R1 and R2 are identical and are —C(O)OR3,
R3 is hydrogen or methyl,
or a salt, hydrate, hydrate of a salt, solvate or solvate of a salt thereof.

* * * * *

UNITED STATES PATENT AND TRADEMARK OFFICE
CERTIFICATE OF CORRECTION

PATENT NO. : 6,962,941 B2
DATED : November 8, 2005
INVENTOR(S) : Martin et al.

It is certified that error appears in the above-identified patent and that said Letters Patent is hereby corrected as shown below:

Column 22,
Line 10, add the following:

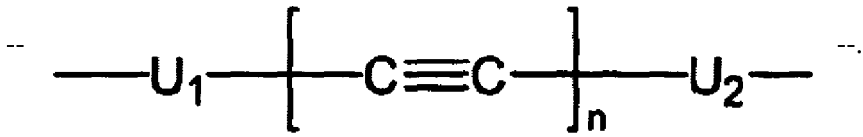

Line 33, delete "1-40-alkyl" and replace with -- 1-4C-alkyl --.

Signed and Sealed this

Twenty-first Day of February, 2006

JON W. DUDAS
*Director of the United States Patent and Trademark Office*